US00PP32315P3

(12) United States Plant Patent
Kurabayashi

(10) Patent No.: US PP32,315 P3
(45) Date of Patent: Oct. 13, 2020

(54) ***RHODODENDRON* PLANT NAMED 'KURACHOUCHOU'**

(50) Latin Name: *Rhododendron hybrid*
Varietal Denomination: Kurachouchou

(71) Applicant: Kabushiki Gaisha Akatsuka Garden Co., Ltd., Tsu-shi, Mie-ken (JP)

(72) Inventor: Yukio Kurabayashi, Tsu (JP)

(73) Assignee: KABUSHIKI GAISHA AKATSUKA GARDEN CO., LTD., Tsu-Shi, Mie-Ken (JP)

( * ) Notice: Subject to any disclaimer, the term of this patent is extended or adjusted under 35 U.S.C. 154(b) by 0 days.

(21) Appl. No.: 16/501,341

(22) Filed: Mar. 28, 2019

(65) Prior Publication Data

US 2019/0394917 P1 Dec. 26, 2019

(30) Foreign Application Priority Data

Jun. 20, 2018 (JP) ..... PBR 33199

(51) Int. Cl.
*A01H 5/02* (2018.01)
*A01H 6/36* (2018.01)

(52) U.S. Cl.
USPC ..... Plt./238
CPC ..... *A01H 6/364* (2018.05)

(58) Field of Classification Search
USPC ..... Plt./238, 239, 240
CPC ..... A01H 5/02; A01H 5/00
See application file for complete search history.

*Primary Examiner* — Kent L Bell
(74) *Attorney, Agent, or Firm* — Cantor Colburn LLP

(57) ABSTRACT

The present invention relates to a new and distinct variety of plant named 'Kurachouchou'. The variety is botanically identified as *Rhododendron* hybrid. The new variety is distinguished from other varieties by a number of properties, including but not limited to, corolla lobe color.

4 Drawing Sheets

Latin name of the plant claimed: The variety is botanically identified as *Rhododendron* hybrid.

CROSS-REFERENCE TO RELATED APPLICATION

This application claims benefit of Japanese Plant Variety Protection Application No. 33199, filed on Jun. 20, 2018, which is incorporated herein in its entirety.

BACKGROUND OF THE INVENTION

The new variety 'Kurachouchou' originated from the controlled cross of the plants 'Stardust' and 'Pink Ice' performed in April 2012. In 2015, the new variety having late blooming, healthy pink rimmed flowers with beautiful color and shape was discovered and selected by the Inventor as a single flowering plant within the progeny of the stated controlled cross-pollination in Anoucho, Tsu-shi, Mie-ken, Japan. As a result of tissue cultures in 2015 and trial production in the field, 'Kurachouchou' was determined as being an excellent variety with beautiful blooms in May 2018, and breeding was completed.

SUMMARY

The present invention relates to a new and distinct variety of plant named 'Kurachouchou'. The variety is botanically identified as *Rhododendron* hybrid. The new variety is distinguished from other varieties by a number of characteristics as set forth below.

When compared to the 'Mrs. Fujii' (not patented) variety having blossoms with a primary color that is pale pink, almost white (R.H.S. color chart N74D) and a secondary color that is a very pale purple (R.H.S. color chart 76D), the new variety of the present invention has been found to exhibit attractive blossoms with a principle strong purplish red color (R.H.S. color chart 71C) and a secondary color that is very light purple (R.H.S. color chart 76B). The annual blooming time for 'Kurachouchou' is one month later than 'Mrs. Fujii'. 'Kurachouchou' has larger leaves (about 11 centimeters (cm) in length and about 4.0 cm in width) compared to 'Mrs. Fujii' (about 10 cm in length and about 2.5 cm in width). The branch color of a one-year old plant of 'Kurachouchou' is dark green (R.H.S. color chart 152A), whereas the branch color of a one-year old plant of 'Mrs. Fujii' is dark red purple, almost brown (R.H.S. color chart 180A). 'Kurachouchou' has a smaller truss size (about 18 cm in diameter and about 18 cm in height) than 'Mrs. Fujii' (about 25 cm in diameter and about 20 cm in height). 'Kurachouchou' has more corolla per truss, about 20, than 'Mrs. Fujii', about 15, and the size of the corolla of 'Kurachouchou' is smaller (about 7 cm in length, about 7 cm in height, and about 6 cm in thickness) than 'Mrs. Fujii' (about 10 cm in length, about 10 cm in height, and about 5 cm in thickness).

'Kurachouchou' can be compared to its female parent 'Stardust' (not patented), and its male parent 'Pink Ice' (not patented). 'Stardust' has a height of about 80 cm and has spotted, light-purple flowers that bloom on April 20. 'Pink Ice' has a height of about 200 cm and pale pink flowers without spots that bloom on April 10. In contrast, 'Kurachouchou' has a height of about 40-50 cm and flowers with a principle strong purplish red color (R.H.S. color chart 71C), a secondary color that is very light purple (R.H.S. color chart 76B), and weak, independent spots (R.H.S. color chart 71B), which bloom on May 5.

'Kurachouchou' can also be compared to its sibling cultivars, 'Triton' (U.S. patent application Ser. No. 16/501,340) and 'Kurachiffon' (U.S. patent application Ser. No. 15/501,342). 'Triton' blooms earlier than 'Kurachouchou', April 1 versus May 5, respectively. 'Triton' flowers have a principle deep purplish pink color (R.H.S. color chart N74C), without spots, and 'Kurachouchou' flowers have a principle purplish red (R.H.S. color chart 71C), a secondary color that is very light purple (R.H.S. color chart 76B), and weak, independent spots (R.H.S. color chart 71B). 'Kurachouchou' blooms later than 'Kurachiffon', May 5 versus April 15. 'Kurachouchou' flowers have a principle strong purplish red color (R.H.S. color chart 71C), with a very light purple (R.H.S. color chart 76B) secondary color and weak, and independent spots (R.H.S. color chart 71B), and 'Kurachiffon' flowers have a principle color that is a light reddish purple (R.H.S. color chart N75A), a secondary color that is very pale purple (R.H.S. color chart 76C), and weak, independent spots (R.H.S. color chart N74B).

BRIEF DESCRIPTION OF THE DRAWINGS

The accompanying photographs show typical specimens of the new variety, including foliage and flowers, in color as nearly true as it is reasonably possible to make in color illustrations of these characteristics.

DESCRIPTION OF THE VARIETY

Figure 1:
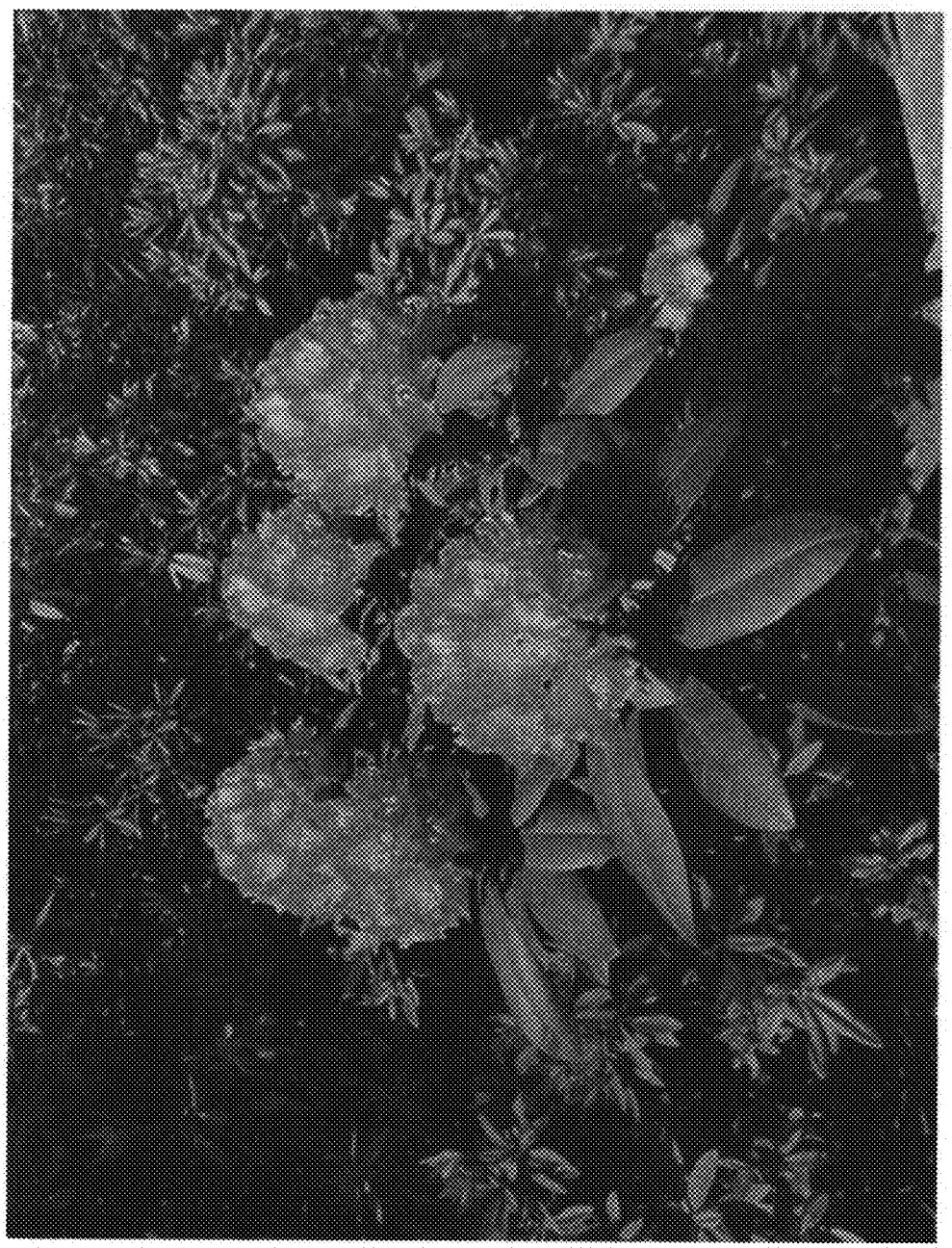
FIG. 1 illustrates the upper side of the flowers and the plant.
Figure 2:
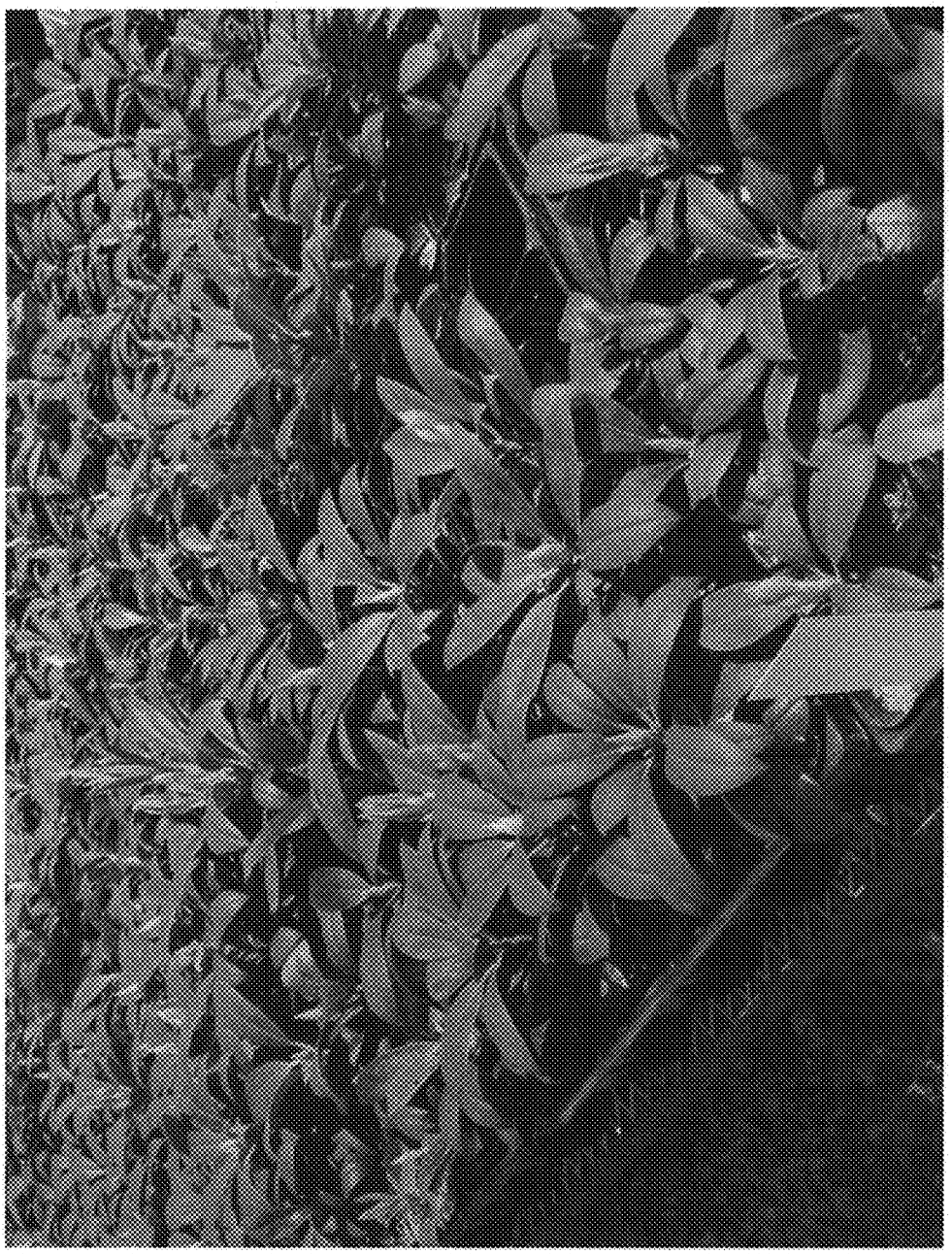
FIG. 2 illustrates a full view of the cultivation area showing the leaves of the plant.
Figure 3:
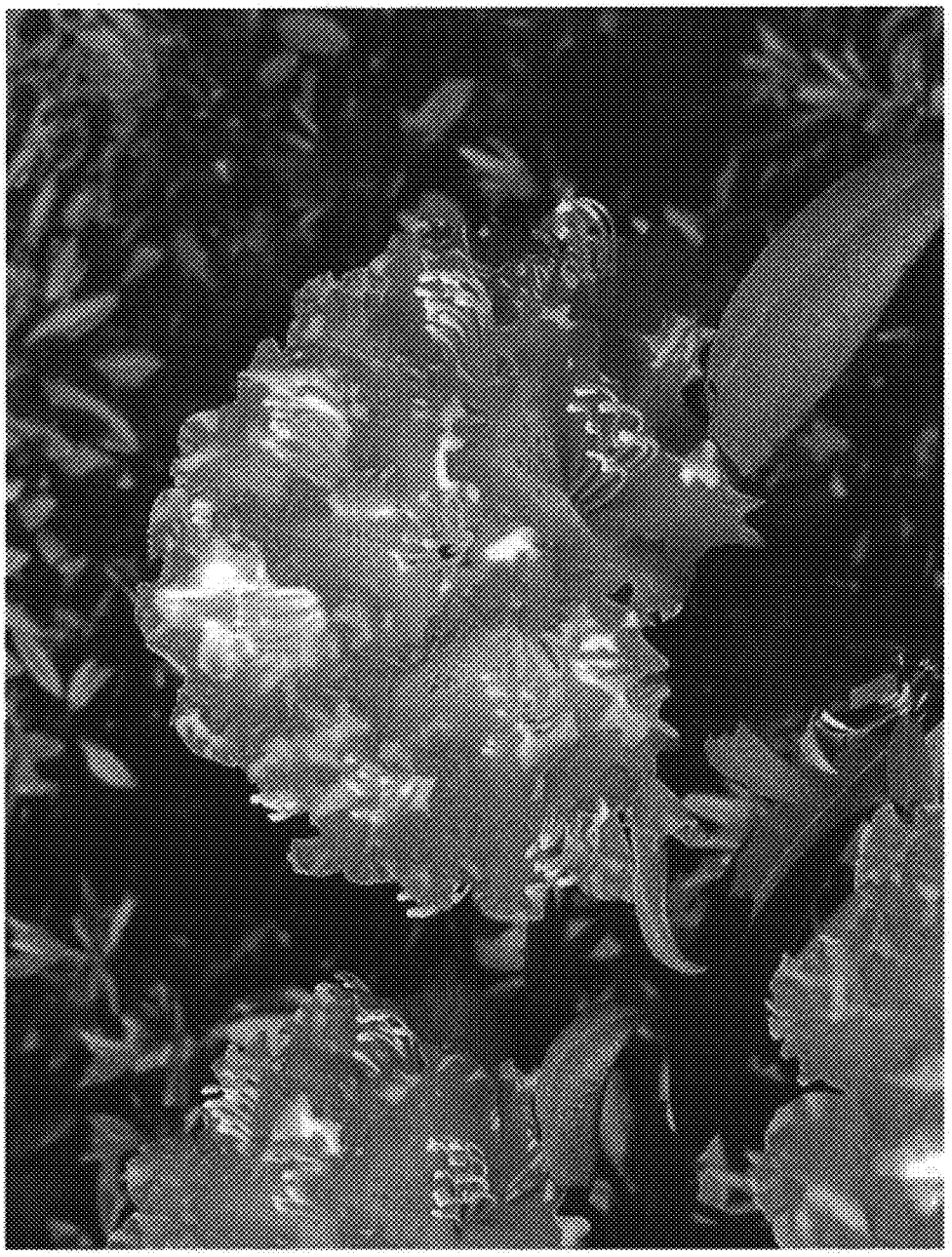
FIG. 3 illustrates a close-up of the flower.
Figure 4:
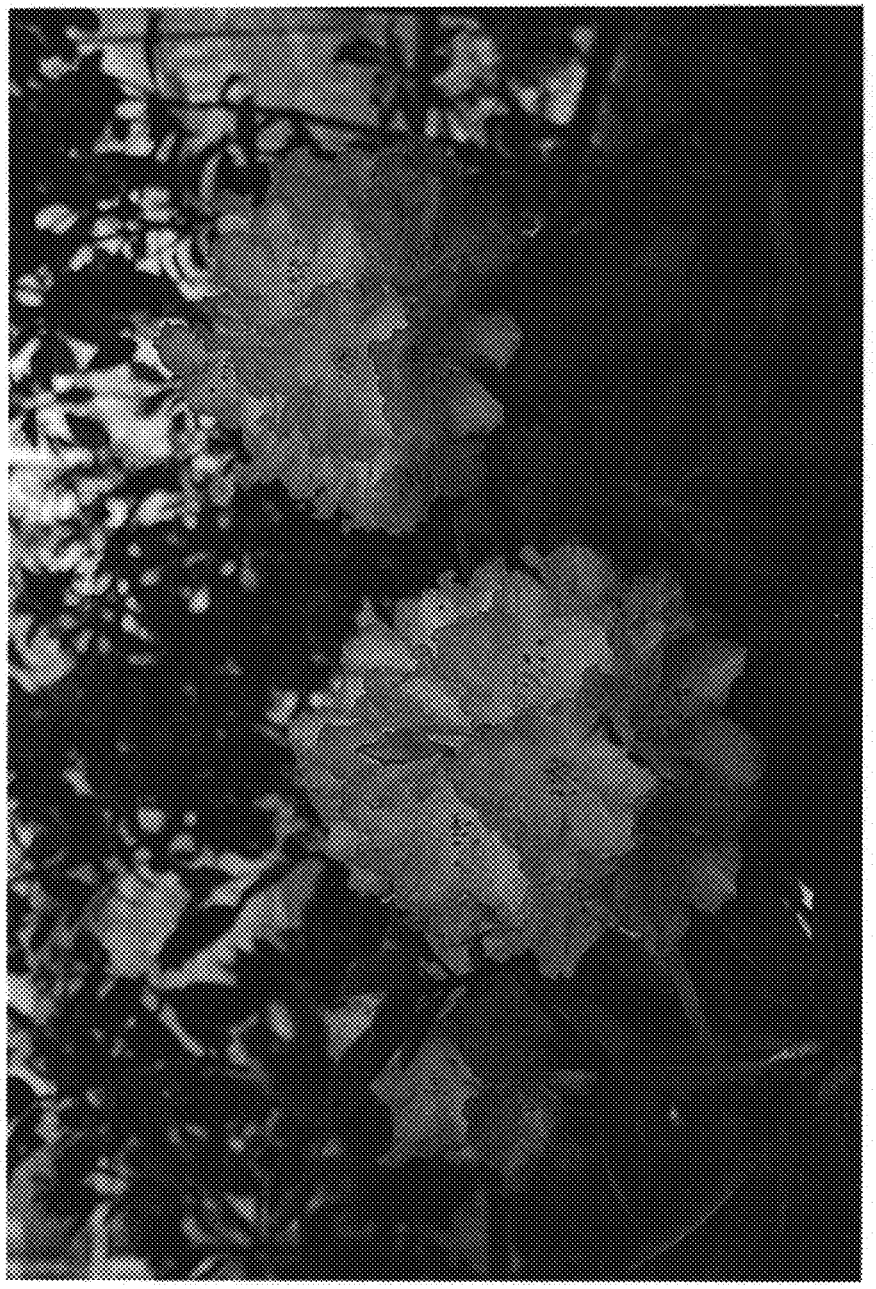
FIG. 4 illustrates, for comparison, the upper side of the flowers and the plant of 'Mrs. Fujii'.

The following detailed description of the new variety is based upon observations taken of plants grown in Anoucho, Tsu-shi, Mie-ken, Japan. Observations of 'Kurachouchou' were taken during the 2015 growing season.

In the following description, color references are made to The Royal Horticultural Society (R.H.S.) Color Chart, except where general terms of ordinary dictionary significance are used.

Botanical classification: *Rhododendrum* hybrid.

Principle use: Flowering shrub for potted plant and open-field cultivation.

Parentage: The female parent is 'Stardust', and the male parent 'Pink Ice'.

Propagation: The new variety was propagated using tissue cultures from plants potted in greenhouse facilities in Anoucho, Tsu-shi, Mie-ken, Japan. Growth points were collected from lateral buds of shoots, and cultivation and growth were performed without using calli.

Plant:

*Size*.—At 3 years of age, plants of the new variety commonly exhibit a height of about 40-50 cm and a width of about 30 cm.

*Habit*.—Vigorous and compact.

Foliage:

*Arrangement*.—Foliage arrangements are pseudoverticillate or false verticillate, appearing whorled or verticillate, but not actually so.

*Type*.—Evergreen flowering shrub, simple lanceolate leaves with an obtuse leaf base, oblong body, acute apex, and obtuse margins. The upper surfaces of the leaves appear semi-glossy, and the bottom surfaces of the leaves appear matte.

*Venation*.—Leaves have a netted (reticulate) venation pattern. R.H.S. color chart 144D on the upper surface of the leaves, and R.H.S. color chart 144D on the bottom surface.

*Size*.—Mature leaves growing midway up the stem commonly are approximately 11 cm in length and approximately 4.0 cm in width.

*Color*.—R.H.S. color chart NN137B on the upper surface, and R.H.S. color chart 143C on the under surface.

Petioles:

*Size*.—2.0 cm in length, and 3.0 mm in diameter.

*Texture*.—Rough with bristles.

*Color*.—R.H.S. color chart 58B.

Branches:

*Size*.—Mature lateral branches (one-year old wood) are 1.5 meter (m) in length and 7.0 mm in diameter.

*Internode length*.—Mature lateral branches (one year old wood) have a 1.0 cm internode length.

*Texture*.—Mature lateral branches (one year old wood) are rough with bristles.

*Color*.—Mature lateral branches (one-year old wood) — R.H.S. color chart 152A.

Peduncles:.

*Size*.—Approximately 3.0 cm in length and 2.5 mm in diameter.

*Color*.—R.H.S. color chart 137C.

Petals:

*Shape*.—Petals are generally wavy with a connected base and sharply pointed apex.

*Size*.—Approximately 5.0 cm in length and 3.0 cm in width.

*Texture*.—Both surfaces of the petals are generally smooth.

Sepals: None.

Flowers:

*Period*.—Blooms approximately May 5 in the evening when cultured at Anoucho, Tsu-shi, Mie-ken, Japan.

*Appearance*.—Corymb.

*Arrangement*.—Spheroidal.

*Truss shape*.—Generally a sphere.

*Truss size*.—Approximately 18 cm diameter, and approximately 18 cm in height.

*Corolla per truss*.—Approximately 20.

*Corolla shape*.—Open funnel shape.

*Corolla size*.—Approximately 7 cm in length, 7 cm in width, and 6 cm in thickness.

*Number of lobes*.—Five lobes per floret.

*Margin of lobes*.—Wavy to frilly.

*Fragrance*.—None.

*Calyx size*.—Approximately 2 millimeters (mm) in length.

*Flower bud shape*.—Lacrimoid.

*Flower bud size*.—Approximately 4.0 mm in length and 2.5 cm in diameter.

*Flower bud color*.—R.H.S. color chart 71B.

*Flower color*.—Two colors on the surfaces of the corolla lobe, with the same color on both the upper and lower surfaces. The principle color on the surfaces of the corolla lobe is strong purplish red (R.H.S. color chart 71C). The secondary color on the surfaces of the corolla lobe is very light purple (R.H.S. color chart 76B). Weak, independent spots (R.H.S. color chart 71B) are present on the throat of the corolla lobe.

*Longevity.*—10 days.

Reproductive organs:

*Stamen number.*—10.

*Filament length.*—Approximately 3.5 cm.

*Filament color.*—R.H.S. color chart 65D.

*Anther shape.*—Barrel shaped.

*Anther length.*—Approximately 2.0 mm.

*Anther color.*—R.H.S. color chart 155A.

*Pollen amount and color.*—High pollen count and R.H.S. color chart 155A.

*Pistil length.*—Approximately 3.0 cm.

*Stigma shape.*—Captiform.

*Stigma color.*—R.H.S. color chart 159A.

*Style length.*—Approximately 2.5 cm.

*Style color.*—R.H.S. color chart 157D.

*Ovary color.*—R.H.S. color chart 178A.

Winter hardiness: Has survived winters with temperatures as low as −3° C. in Anoucho, Tsu-shi, Mie-ken, Japan.

Disease resistance: During observations to date, the foliage has been disease resistant. Although generally, *Rhododendron* hybrid plants are prone to root rot disease, which tends to occur in high temperatures, 'Kurachouchou' is resistant to root rot because it is resistant to high temperatures.

Successive generations: Reproduces true to type in successive generations as set forth above.

What is claimed is:

1. A new and distinct variety of *Rhododendron* hybrid plant, substantially as shown and described.

* * * * *